(12) United States Patent
Lee et al.

(10) Patent No.: US 11,969,019 B2
(45) Date of Patent: Apr. 30, 2024

(54) AEROSOL GENERATING APPARATUS USING INDUCTION HEATING METHOD AND AEROSOL GENERATING METHOD USING INDUCTION HEATING METHOD

(71) Applicant: KT&G CORPORATION, Daejeon (KR)

(72) Inventors: Seung Won Lee, Gwangmyeong-si (KR); Sang Kyu Park, Hwaseong-si (KR)

(73) Assignee: KT&G CORPORATION, Daejeon (KR)

( * ) Notice: Subject to any disclaimer, the term of this patent is extended or adjusted under 35 U.S.C. 154(b) by 712 days.

(21) Appl. No.: 17/056,137

(22) PCT Filed: Nov. 15, 2019

(86) PCT No.: PCT/KR2019/015594
§ 371 (c)(1),
(2) Date: Nov. 17, 2020

(87) PCT Pub. No.: WO2020/116811
PCT Pub. Date: Jun. 11, 2020

(65) Prior Publication Data
US 2021/0219617 A1    Jul. 22, 2021

(30) Foreign Application Priority Data
Dec. 6, 2018 (KR) .......... 10-2018-0156280

(51) Int. Cl.
*A24F 40/465* (2020.01)
*A24F 40/60* (2020.01)
*H05B 6/10* (2006.01)

(52) U.S. Cl.
CPC ............ *A24F 40/465* (2020.01); *A24F 40/60* (2020.01); *H05B 6/108* (2013.01)

(58) Field of Classification Search
CPC ........ A24F 40/465; A24F 40/60; A24F 40/50; A24F 40/20; H05B 6/108; H05B 6/06;
(Continued)

(56) References Cited

U.S. PATENT DOCUMENTS 5,613,505 A    3/1997 Campbell et al.
10,477,894 B2  11/2019 Mironov
(Continued)

FOREIGN PATENT DOCUMENTS

CN    106455713 A    2/2017
CN    107708453 A    2/2018
(Continued)

OTHER PUBLICATIONS

Extended European Search Report dated Nov. 2, 2021 in Application No. 19892115.7.
(Continued)

*Primary Examiner* — Abdullah A Riyami
*Assistant Examiner* — Nader J Alhawamdeh
(74) *Attorney, Agent, or Firm* — Sughrue Mion, PLLC

(57) ABSTRACT

An embodiment of the present invention includes a plurality of coils which have different numbers of windings and generate an alternating magnetic field when alternating current is applied; a susceptor for generating an aerosol by heating adjacent aerosol-generating substrates using heat generated through the alternating magnetic fields generated from the plurality of coils; and a controller for controlling a predetermined alternating current to be supplied to each of the plurality of coils, wherein the controller controls a first portion and a second portion of the susceptor to be heated differentially by alternating current supplied to the plurality of coils.

14 Claims, 12 Drawing Sheets

(58) Field of Classification Search
CPC . H05B 6/40; H05B 6/105; H05B 6/36; A61M 11/042; A61M 2205/0211; A61M 15/06; A61M 2205/3368; A61M 2205/7545; A61M 2205/36; A61M 2205/8206; H03K 17/223

See application file for complete search history.

(56) References Cited

U.S. PATENT DOCUMENTS

| | | | |
|---|---|---|---|
| 11,019,848 | B2 | 6/2021 | Rojo-Calderon |
| 11,033,055 | B2 | 6/2021 | Fraser et al. |
| 2016/0374397 | A1 | 12/2016 | Jordan et al. |
| 2017/0079330 | A1 | 3/2017 | Mironov et al. |
| 2017/0086508 | A1* | 3/2017 | Mironov ............... A24C 5/01 |
| 2017/0172208 | A1* | 6/2017 | Mironov ............... H05B 6/108 |
| 2018/0027884 | A1* | 2/2018 | Zuber ............... A61M 15/0036 |
| 2018/0029782 | A1* | 2/2018 | Zuber ............... H05B 1/0227 |
| 2018/0125119 | A1 | 5/2018 | Cadieux et al. |
| 2018/0192700 | A1 | 7/2018 | Fraser et al. |
| 2018/0310622 | A1* | 11/2018 | Mironov ............... A24D 1/20 |
| 2019/0053541 | A1 | 2/2019 | Rojo-Calderon |
| 2019/0320720 | A1 | 10/2019 | Mironov et al. |

FOREIGN PATENT DOCUMENTS

| | | |
|---|---|---|
| CN | 108135276 A | 6/2018 |
| CN | 208016042 U | 10/2018 |
| EP | 4 266 831 A2 | 10/2023 |
| JP | 2018-524983 A | 9/2018 |
| KR | 10-0385395 B1 | 8/2003 |
| KR | 10-1667177 B1 | 10/2016 |
| KR | 10-2017-0007235 A | 1/2017 |
| KR | 10-2018-0069895 A | 6/2018 |
| KR | 10-2018-0073626 A | 7/2018 |
| WO | 95/27411 A1 | 10/1995 |
| WO | 2017/001818 A1 | 1/2017 |
| WO | 2017/068098 A1 | 4/2017 |
| WO | 2018/073376 A1 | 4/2018 |
| WO | 2018/138072 A1 | 8/2018 |
| WO | 2018/206616 A1 | 11/2018 |

OTHER PUBLICATIONS

Office Action issued from Korean Patent Application No. 10-2018-0156280 dated Jun. 18, 2020.
International Search Report for PCT/KR2019/015594 dated Feb. 27, 2020 (PCT/ISA/210).
Communication dated Aug. 17, 2021, issued by the Japanese Patent Office in application No. 2020-542826.
Chinese Office Action dated Feb. 11, 2023 in Chinese Application No. 201980034286.6.
Notification of Reason for Refusal dated Dec. 24, 2020 from the Korean Intellectual Property Office in KR Application No. 10-2018-0156280.
Extended European search report dated Nov. 3, 2023 in Application No. 23190747.8.

* cited by examiner

AEROSOL GENERATING APPARATUS USING INDUCTION HEATING METHOD AND AEROSOL GENERATING METHOD USING INDUCTION HEATING METHOD

CROSS REFERENCE TO RELATED APPLICATIONS

This application is a National Stage of International Application No. PCT/KR2019/015594 filed Nov. 15, 2019, claiming priority based on Korean Patent Application No. 10-2018-0156280 filed Dec. 6, 2018.

TECHNICAL FIELD

The present invention relates to an aerosol-generating device using induction heating and a method of generating an aerosol using induction heating, and more particularly, to an aerosol-generating device and a method of generating an aerosol by using a phenomenon in which material constituting a susceptor is heated by an alternating magnetic field generated by alternating current flowing through a coil such as an inductor.

BACKGROUND ART

Recently, the demand for alternative ways of overcoming the disadvantages of traditional cigarettes has increased. For example, there is growing demand for a method of generating aerosol by heating an aerosol generating material in cigarettes, rather than by combusting cigarettes. Accordingly, research into a heating-type cigarette and a heating-type aerosol generator has been actively conducted.

DESCRIPTION OF EMBODIMENTS

Technical Problem

The technical problem to be solved by the present invention is to provide an aerosol-generating device capable of uniformly heating a cigarette containing an aerosol-generating substrate through induction heating and a method of driving the aerosol-generating device.

Solution to Problem

A device according to an embodiment of the present invention for solving the above technical problem, may include a plurality of coils which have different numbers of windings and generate an alternating magnetic field when alternating current is applied; a susceptor for generating an aerosol by heating adjacent aerosol-generating substrates using heat generated through the alternating magnetic fields generated from the plurality of coils; and a controller for controlling a predetermined alternating current to be supplied to each of the plurality of coils, wherein the controller controls a first portion and a second portion of the susceptor to be heated differentially by alternating current supplied to the plurality of coils.

A method according to an embodiment of the present invention for solving the above technical problem, may include generating alternating magnetic fields by a controller controlling alternating current to be supplied to a plurality of coils having different winding numbers; and a susceptor being inductively heated by the alternating magnetic field and heating an adjacent aerosol-generating substrate, wherein the heating of an adjacent aerosol-generating substrate may include differentially heating a first portion and a second portion of the susceptor by alternating current supplied to the plurality of coils.

Advantageous Effects of Disclosure

According to the present invention, when a user smokes using an aerosol-generating device operating according to an induction heating method, it is possible to provide a consistent feeling of smoking to the user.

BEST MODE

Figure 1:
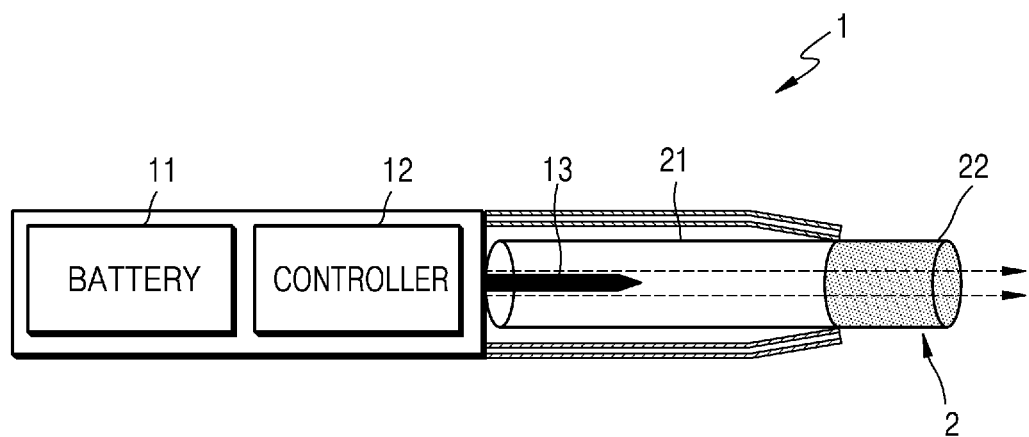
FIGS. 1 through 3 are diagrams showing examples in which a cigarette is inserted into an aerosol-generating device.

A device according to an embodiment of the present invention for solving the above technical problem, may include a plurality of coils which have different numbers of windings and generate alternating magnetic fields when an alternating current is applied; a susceptor configured to generate an aerosol by heating adjacent aerosol-generating substrates using heat generated through the alternating magnetic fields generated from the plurality of coils; and a controller configured to control a predetermined alternating current to be supplied to the plurality of coils, such that a first portion and a second portion of the susceptor are heated differentially by the predetermined alternating current.

In the device, the susceptor may further include a third portion in addition to the first portion and the second portion, the first portion, the second portion, and the third portion are continuously connected, and the plurality of coils are arranged so that the first portion and the third portion are differentially heated from the second portion.

In the device, the first portion and the third portion are heated by an alternating magnetic field generated from a first coil having a predetermined interval with zero windings, and the second portion is heated by an alternating magnetic field generated from a second coil arranged in the interval.

In the device, the controller stops supplying the alternating current to the first coil when a predetermined time has elapsed after controlling so that the alternating current is supplied to the first coil and the second coil.

In the device, at least two of the plurality of coils are arranged to overlap in a specific direction from the first portion so that the first portion is heated according to alternating magnetic fields generated by the two coils.

In the device, the plurality of coils include a first coil and a second coil, and a ratio of a length of the second coil to a length of the first coil is equal to or less than a preset value.

In the device, the controller controls alternating current to be supplied to the plurality of coils at different time points through a field-effect transistor (FET).

A method according to an embodiment of the present invention for solving the above technical problem, may include generating alternating magnetic fields by a controller controlling an alternating current to be supplied to a plurality of coils having different winding numbers; and heating an adjacent aerosol-generating substrate by a susceptor that is inductively heated by the alternating magnetic fields, wherein the heating of the adjacent aerosol-generating substrate includes differentially heating a first portion and a second portion of the susceptor by the alternating current supplied to the plurality of coils.

In the method, the susceptor may further include a third portion in addition to the first portion and the second portion, the first portion, the second portion and the third portion are continuously connected, and the heating of an adjacent aerosol-generating substrate may include the plurality of coils heating the first portion and the third portion differentially from the second portion.

In the method, the heating of an adjacent aerosol-generating substrate may include heating the first portion and the third portion based on the alternating current being supplied to a first coil having a predetermined interval with zero windings; and heating the second portion based on the alternating current being supplied to a second coil arranged in the interval.

The method may further include stopping supply of alternating current to the first coil when a predetermined time has elapsed after the alternating current is supplied to the first coil and the second coil.

In the method, the heating of an adjacent aerosol-generating substrate may include heating the first portion according to alternating magnetic fields generated by the plurality of coils arranged to overlap in a specific direction from the first portion.

In the method, the plurality of coils may include a first coil and a second coil, and a ratio of a length of the second coil to a length of the first coil is equal to or less than a preset value.

In the method, the generating of alternating magnetic fields may include supplying alternating current to the plurality of coils at different time points through a field-effect transistor (FET).

MODE OF DISCLOSURE

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. Also, specified terms may be selected by the applicant, and in this case, the detailed meaning thereof will be described in the detailed description of the disclosure. Thus, the terms used in the present disclosure should be understood not as simple names but based on the meaning of the terms and the overall description of the present disclosure.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

Hereinafter, embodiments of the present disclosure will be described in detail with reference to the drawings.

Figure 2:
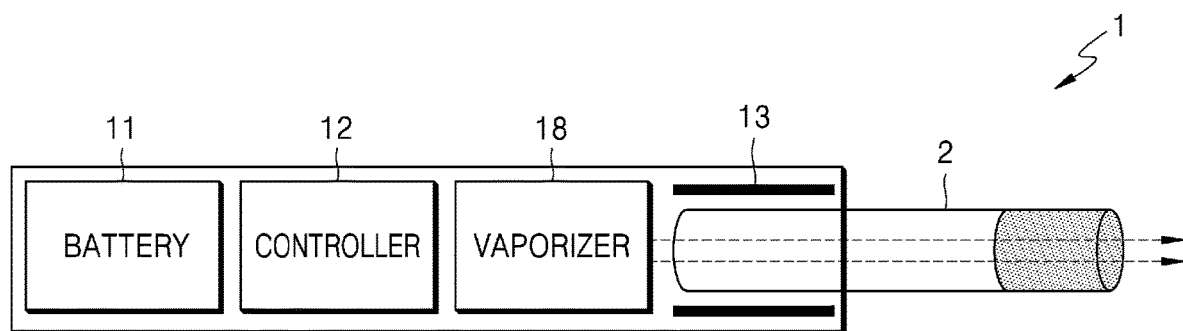
Figure 3:
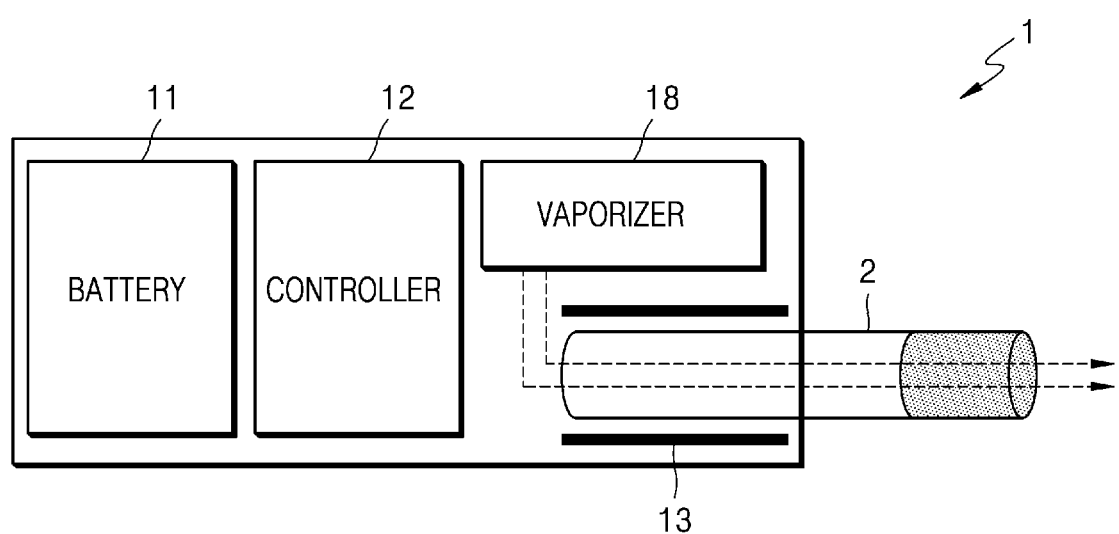

FIGS. 1 through 3 are diagrams showing examples in which a cigarette is inserted into an aerosol-generating device.

Referring to FIG. 1, an aerosol generator 1 includes a battery 11, a controller 12, and a heater 13. Referring to FIG. 2 and FIG. 3, the aerosol generator 1 further includes a vaporizer 18. Also, a cigarette 2 may be inserted into an inner space of the aerosol generator 1.

The elements related to the embodiment are illustrated in the aerosol generator 1 of FIGS. 1 to 3. Therefore, one of ordinary skill in the art would appreciate that other universal elements than the elements shown in FIGS. 1 to 3 may be further included in the aerosol generator 1.

Also, FIGS. 2 and 3 show that the aerosol generator 1 includes the heater 13, but if necessary, the heater 13 may be omitted.

In FIG. 1, the battery 11, the controller 12, and the heater 13 are arranged in a row. Also, FIG. 2 shows that the battery 11, the controller 12, the vaporizer 18, and the heater 13 are arranged in a row. Also, FIG. 3 shows that the vaporizer 18 and the heater 13 are arranged in parallel with each other. However, an internal structure of the aerosol generator 1 is not limited to the examples shown in FIGS. 1 to 3. That is, according to a design of the aerosol generator 1, arrangement of the battery 11, the controller 12, the heater 13, and the vaporizer 18 may be changed.

When the cigarette 2 is inserted into the aerosol generator 1, the aerosol generator 1 operates the heater 13 and/or the vaporizer 18 to generate aerosol from the cigarette 2 and/or the vaporizer 18. The aerosol generated by the heater 13 and/or the vaporizer 18 may be transferred to a user via the cigarette 2.

If necessary, even when the cigarette 2 is not inserted in the aerosol generator 1, the aerosol generator 1 may heat the heater 13.

The battery 11 supplies the electric power used to operate the aerosol generator 1. For example, the battery 11 may supply power for heating the heater 13 or the vaporizer 18 and supply power for operating the controller 12. In addition, the battery 11 may supply power for operating a display, a sensor, a motor, and the like installed in the aerosol generator 1.

The controller 12 controls the overall operation of the aerosol generator 1. In detail, the controller 12 may control operations of other elements included in the aerosol generator 1, as well as the battery 11, the heater 13, and the vaporizer 18. Also, the controller 12 may check the status of each component in the aerosol generator 1 to determine whether the aerosol generator 1 is in an operable state.

The controller 12 includes at least one processor. A processor can be implemented as an array of a plurality of logic gates or can be implemented as a combination of a general-purpose microprocessor and a memory in which a program executable in the microprocessor is stored. It will be understood by one of ordinary skill in the art that the present disclosure may be implemented in other forms of hardware.

The heater 13 may be heated by the electric power supplied from the battery 11. For example, when the cigarette is inserted in the aerosol generator 1, the heater 13 may be located outside the cigarette. Therefore, the heated heater 13 may raise the temperature of an aerosol generating material in the cigarette.

The heater 13 may be an electro-resistive heater. For example, the heater 13 includes an electrically conductive track, and the heater 13 may be heated as a current flows through the electrically conductive track. However, the heater 13 is not limited to the above example, and any type of heater may be used provided that the heater is heated to a desired temperature. Here, the desired temperature may be set in advance on the aerosol generator 1, or may be set by a user.

In addition, in another example, the heater 13 may include an induction heating type heater. In detail, the heater 13 may include an electrically conductive coil for heating the cigarette in an induction heating method, and the cigarette may include a susceptor that may be heated by the induction heating type heater.

For example, the heater 13 may include a tubular type heating element, a plate type heating element, a needle type heating element, or a rod type heating element, and may heat the inside or outside of the cigarette 2 according to the shape of the heating element.

Also, there may be a plurality of heaters 13 in the aerosol generator 1. Here, the plurality of heaters 13 may be arranged to be inserted into the cigarette 2 or on the outside of the cigarette 2. Also, some of the plurality of heaters 13 may be arranged to be inserted into the cigarette 2 and the other may be arranged on the outside of the cigarette 2. In addition, the shape of the heater 13 is not limited to the example shown in FIGS. 1 to 3, but may be manufactured in various shapes.

The vaporizer 18 may generate aerosol by heating a liquid composition and the generated aerosol may be delivered to the user after passing through the cigarette 2. In other words, the aerosol generated by the vaporizer 18 may move along an air flow passage of the aerosol generator 1, and the air flow passage may be configured for the aerosol generated by the vaporizer 18 to be delivered to the user through the cigarette.

For example, the vaporizer 18 may include a liquid storage unit, a liquid delivering unit, and a heating element, but is not limited thereto. For example, the liquid storage unit, the liquid delivering unit, and the heating element may be included in the aerosol generator 1 as independent modules.

The liquid storage may store a liquid composition. For example, the liquid composition may be a liquid including a tobacco containing material including a volatile tobacco flavor component, or a liquid including a non-tobacco material. The liquid storage unit may be detachable from the vaporizer 18 or may be integrally manufactured with the vaporizer 18.

For example, the liquid composition may include water, solvents, ethanol, plant extracts, flavorings, flavoring agents, or vitamin mixtures. The flavoring may include, but is not limited to, menthol, peppermint, spearmint oil, various fruit flavoring ingredients, etc. The flavoring agent may include components that may provide the user with various flavors or tastes. Vitamin mixtures may be a mixture of at least one of vitamin A, vitamin B, vitamin C, and vitamin E, but are not limited thereto. Also, the liquid composition may include an aerosol former such as glycerin and propylene glycol.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

The heating element is an element for heating the liquid composition delivered by the liquid delivering unit. For example, the heating element may be a metal heating wire, a metal hot plate, a ceramic heater, or the like, but is not limited thereto. In addition, the heating element may include a conductive filament such as nichrome wire and may be positioned as being wound around the liquid delivery element. The heating element may be heated by a current supply and may transfer heat to the liquid composition in contact with the heating element, thereby heating the liquid composition. As a result, aerosol may be generated.

For example, the vaporizer 18 may be referred to as a cartomizer or an atomizer, but is not limited thereto.

In addition, the aerosol generator 1 may further include universal elements, in addition to the battery 11, the controller 12, the heater 13, and the vaporizer 18. For example, the aerosol generator 1 may include a display capable of outputting visual information and/or a motor for outputting tactile information. In addition, the aerosol generator 1 may include at least one sensor (a puff sensor, a temperature sensor, a cigarette insertion sensor, etc.) Also, the aerosol generator 1 may be manufactured to have a structure, in which external air may be introduced or internal air may be discharged even in a state where the cigarette 2 is inserted.

Although not shown in FIGS. 1 to 3, the aerosol generator 1 may configure a system with an additional cradle. For example, the cradle may be used to charge the battery 11 of the aerosol generator 1. Alternatively, the heater 13 may be heated in a state in which the cradle and the aerosol generator 1 are coupled to each other.

The cigarette 2 may be similar to a typical burning cigarette. For example, the cigarette 2 may include a first portion containing an aerosol generating material and a second portion including a filter and the like. The second portion of the cigarette 2 may also include the aerosol generating material. For example, an aerosol generating material made in the form of granules or capsules may be inserted into the second portion.

The entire first portion may be inserted into the aerosol generator 1 and the second portion may be exposed to the outside. Alternatively, only a portion of the first portion may be inserted into the aerosol generator 1 or the entire first portion and a portion of the second portion may be inserted into the aerosol generator 1. The user may puff aerosol while holding the second portion by the mouth of the user. At this time, the aerosol is generated by as the outside air passes through the first portion, and the generated aerosol passes through the second portion and is delivered to a user's mouth.

For example, the outside air may be introduced through at least one air passage formed in the aerosol generator 1. For example, the opening and closing of the air passage formed in the aerosol generator 1 and/or the size of the air passage may be adjusted by a user. Accordingly, the amount and quality of the aerosol may be adjusted by the user. In another example, the outside air may be introduced into the cigarette 2 through at least one hole formed in a surface of the cigarette 2.

Hereinafter, an example of the cigarette 2 will be described with reference to FIGS. 4 and 5.

Figure 4:
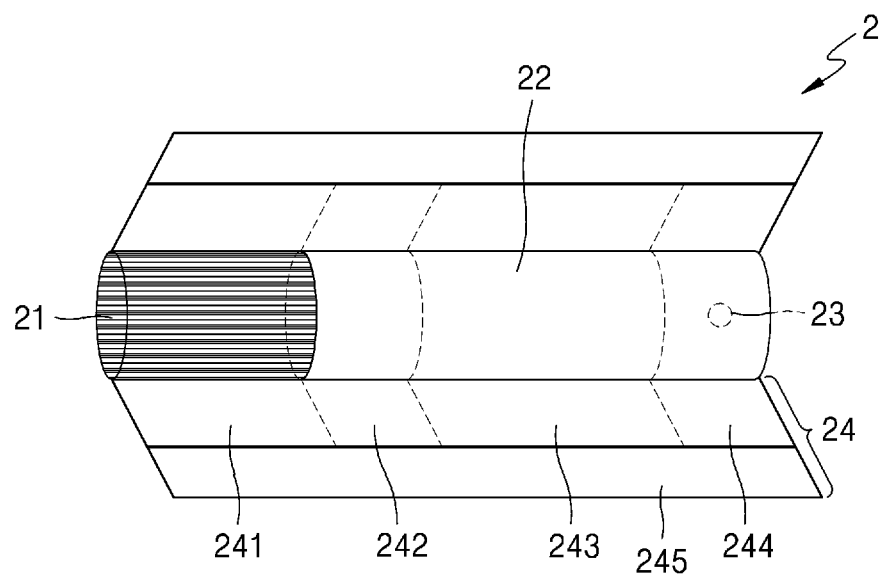
FIGS. 4 and 5 are diagrams showing examples of cigarettes.
Figure 5:
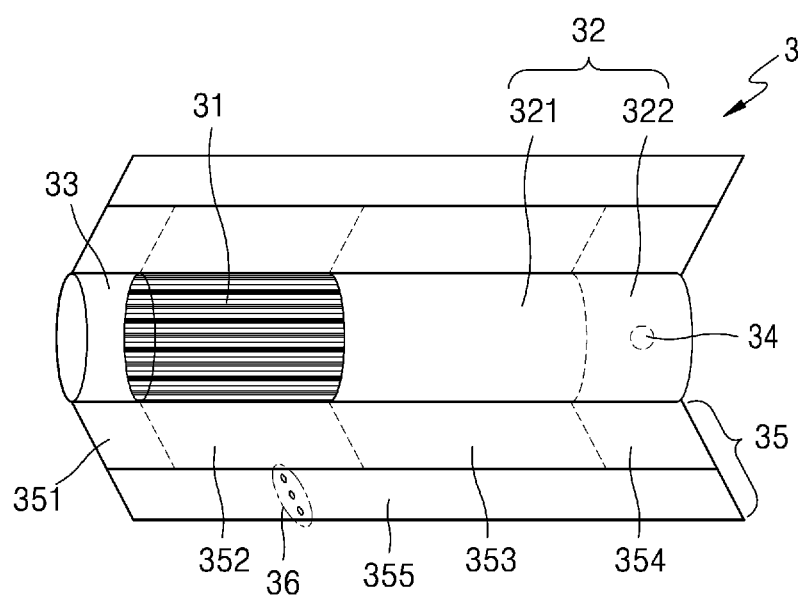

FIGS. 4 and 5 illustrate an example of a cigarette.

Referring to FIG. 4, the cigarette 2 includes a tobacco rod 21 and a filter rod 22. The first portion described above with reference to FIGS. 1 to 3 includes the tobacco rod 21 and the second portion includes the filter rod 22.

In FIG. 4, the filter rod 22 is shown as a single segment, but is not limited thereto. In other words, the filter rod 22 may include a plurality of segments. For example, the filter rod 22 may include a first segment for cooling down the aerosol and a second segment for filtering a predetermined component included in the aerosol. Also, if necessary, the filter rod 22 may further include at least one segment performing another function.

The cigarette 2 may be packaged by at least one wrapper 24. The wrapper 24 may include at least one hole through which the outside air is introduced or inside air is discharged. For example, the cigarette 2 may be packaged by one wrapper 24. In another example, the cigarette 2 may be packaged by two or more wrappers 24. For example, the tobacco rod 21 may be packaged by a first wrapper 241, and the filter rod 22 may be packaged by wrappers 242 to 244. And the entire cigarette 2 may be packaged by another wrapper 245. When the filter rod 22 includes a plurality of segments, each segment may be packaged by separate wrappers 242, 243, and 244.

The tobacco rod 21 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. In addition, the tobacco rod 21 may include other additive materials like a flavoring agent, a wetting agent, and/or an organic acid. Also, a flavoring liquid such as menthol, humectant, etc. may be added to the tobacco rod 21 by being sprayed to the tobacco rod 21.

The tobacco rod 21 may be manufactured variously. For example, the tobacco rod 21 may be fabricated as a sheet or a strand. Also, the tobacco rod 21 may be fabricated by tobacco leaves that are obtained by fine-cutting a tobacco sheet. Also, the tobacco rod 21 may be surrounded by a heat conducting material. For example, the heat-conducting material may be, but is not limited to, a metal foil such as aluminum foil. For example, the heat conducting material surrounding the tobacco rod 21 may improve a thermal conductivity applied to the tobacco rod by evenly dispersing the heat transferred to the tobacco rod 21, and thereby improving tobacco taste. Also, the heat conducting material surrounding the tobacco rod 21 may function as a susceptor that is heated by an inducting heating type heater. Although not shown in the drawings, the tobacco rod 21 may further include a susceptor, in addition to the heat conducting material surrounding the outside thereof.

The filter rod 22 may be a cellulose acetate filter. In addition, the filter rod 22 is not limited to a particular shape. For example, the filter rod 22 may be a cylinder type rod or a tube type rod including a cavity therein. Also, the filter rod 22 may be a recess type rod. When the filter rod 22 includes a plurality of segments, at least one of the plurality of segments may have a different shape from the others.

Also, the filter rod 22 may include at least one capsule 23. Here, the capsule 23 may generate flavor or may generate aerosol. For example, the capsule 23 may have a structure, in which a liquid containing a flavoring material is wrapped with a film. The capsule 23 may have a circular or cylindrical shape, but is not limited thereto.

Referring to FIG. 5, the cigarette 3 may further include a front-end filter 33. The front-end plug 33 may be located on a side of the tobacco rod 31 which is not facing the filter rod 32. The front-end plug 33 may prevent the tobacco rod 31 from being detached and may prevent a liquefied aerosol from flowing from the tobacco rod 31 into an aerosol generating device (1 of FIGS. 1 to 3) during smoking.

The filter rod 32 may include a first segment 321 and a second segment 322. Here, the first segment 321 may correspond to the first segment of the filter rod 22 of FIG. 4, and the second segment 322 may correspond to the third segment of the filter rod 22 of FIG. 4.

The diameter and the total length of the cigarette 3 may correspond to the diameter and the total length of the cigarette 2 of FIG. 4.

The cigarette 3 may be wrapped by at least one wrapper 35. At least one hole through which outside air flows in or inside gas flows out may be formed in the wrapper 35. For example, the front-end plug 33 may be wrapped by a first wrapper 351, the tobacco rod 31 may be wrapped by a second wrapper 352, the first segment 321 may be wrapped by a third wrapper 353, and the second segment 322 may be wrapped by a fourth wrapper 354. Also, the entire cigarette 3 may be re-wrapped by a fifth wrapper 355.

Also, at least one perforation 36 may be formed in the fifth wrapper 355. For example, the perforation 36 may be formed in a region surrounding the tobacco rod 31, but is not limited thereto. The perforation 36 may serve to transfer heat generated by the heater 13 shown in FIGS. 2 and 3 into the tobacco rod 31.

Also, the second segment 322 may include at least one capsule 34. Here, the capsule 34 may serve to generate a flavor or an aerosol. For example, the capsule 34 may have a structure in which a liquid containing perfume is wrapped in a film. The capsule 34 may have a spherical or cylindrical shape, but is not limited thereto.

Figure 6:
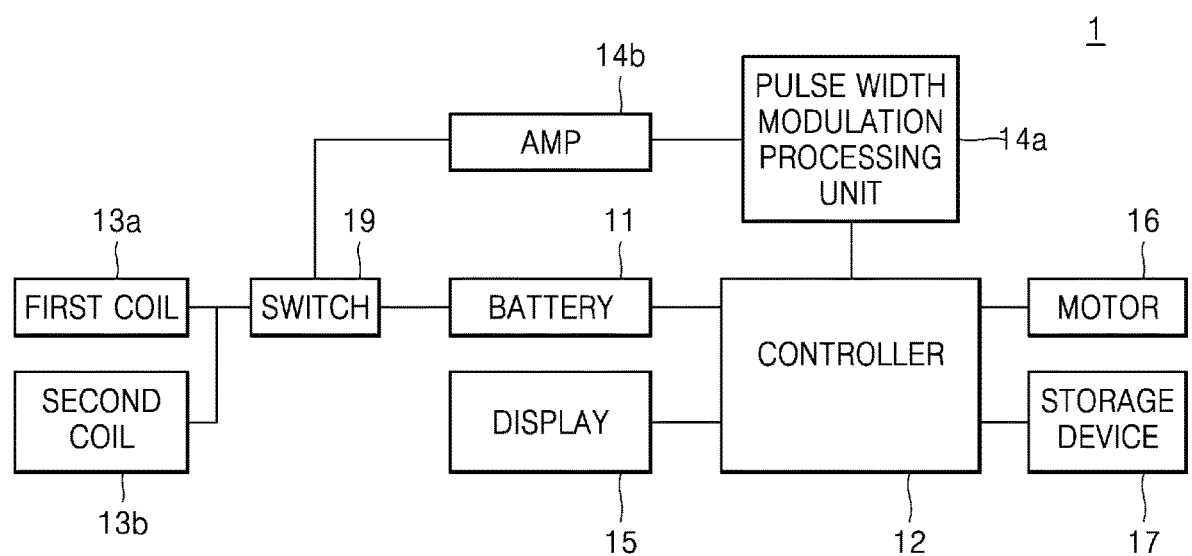
FIG. 6 is a diagram schematically showing a block diagram of an example of an aerosol-generating device according to the present invention.

FIG. 6 is a diagram schematically showing a block diagram of an example of an aerosol-generating device according to the present invention.

Referring to FIG. 6, the aerosol-generating device 1 according to the present invention includes a battery 11, a controller 12, a first coil 13a, a second coil 13b, a pulse width modulation processing unit 14a, an AMP 14b, a display 15, a motor 16, a storage device 17, and a vaporizer 18. Hereinafter, for convenience of description, the general function of each component included in the aerosol-generating device 1 will be first described, and then an operation of the controller 12 according to the embodiment will be described in detail.

The battery 11 supplies power to the first coil 13a and the second coil 13b, and an amount of power supplied to the first coil 13a and the second coil 13b may be adjusted by a control signal generated by the controller 12. Depending on an embodiment, a regulator that maintains a constant voltage of the battery may be included between the battery 11 and the controller 12.

The controller 12 controls overall operations of the battery 11, the first coil 13a, the second coil 13b, the pulse width modulation processing unit 14a, the display 15, the motor 16, the storage device 17 and the vaporizer 18 which are included in the aerosol-generating device 1. Although not shown in FIG. 6, depending on an embodiment, the controller 12 may further include an input receiving unit (not shown) that receives a user's button input or touch input, and a communication unit (not shown) capable of communicating with an external communication device such as a user terminal. In addition, although not shown in FIG. 6, the controller 12 may further include a module for performing proportional integral differential control (PID) on the first coil 13a and the second coil 13b.

When an AC current is supplied to the first coil 13a and the second coil 13b, an alternating magnetic field is generated. A direction and intensity of the alternating magnetic field generated by the first coil 13a and the second coil 13b may vary depending on a direction of the alternating current supplied to the first coil 13a and the second coil 13b and the number of windings of the first coil 13a and the second coil 13b. When alternating current is supplied to the first coil 13a and the second coil 13b to generate an alternating magnetic field, a susceptor material located around the first coil 13a and the second coil 13b is affected by the alternating magnetic field, and the susceptor is heated. This induction heating phenomenon is a well-known phenomenon and may be explained by Faraday's Law of induction and Ohm's Law. According to the induction heating phenomenon means a phenomenon, a changing electric field is generated in a conductor when a magnetic induction in the conductor changes.

As described above, in the present invention, the electric field is generated in the conductor, so that an eddy current flows in the conductor according to Ohm's law. The eddy current generates heat proportional to the current density and resistance of the conductor. The susceptor that generates heat by the alternating magnetic field may heat an aerosol-generating substrate to generate an aerosol when a cigarette containing the aerosol-generating substrate contacts the susceptor.

The pulse width modulation processing unit 14a allows the controller 12 to control the power supplied to the first coil 13a and the second coil 13b by transmitting PWM (Pulse Width Modulation) signals to the first coil 13a and the second coil 13b. Depending on an embodiment, the pulse width modulation processing unit 14a may be implemented to be included in the controller 12, and the PWM signal output from the pulse width modulation processing unit 14a may be a digital PWM signal. In addition, the PWM control signal transmitted from the pulse width modulation processing unit 14a may be amplified according to a preset amplification factor by the AMP 14b.

The display 15 visually outputs various alarm messages generated by the aerosol-generating device 1 so that a user using the aerosol-generating device 1 may check the alarm messages. The user may check the battery power shortage message or the susceptor overheat warning message output to the display 15, and then may stop the operation of the aerosol-generating device 1 or take appropriate measures before the aerosol-generating device 1 is broken.

The motor 16 is driven by the controller 12 so that the user may recognize that the aerosol-generating device 1 is ready for use through tactile sense.

The storage device 17 stores various pieces of information to provide a consistent flavor to the user who uses the aerosol-generating device 1 while appropriately controlling a power supplied to the first coil 13a and the second coil 13b by the controller 12. The storage device 17 may not only be configured as a non-volatile memory, such as a flash memory, but also may be configured as a volatile memory that temporarily stores data only when power is supplied in order to secure a faster data input/output (I/O) speed.

The vaporizer 18 may generate an aerosol by heating a liquid composition, and the generated aerosol may be delivered to the user through a cigarette 2. As described in FIGS. 2 and 3, the vaporizer 18 may include a liquid storage, a liquid delivery element, and a heating element. In particular, the vaporizer 18 may include a heating element for heating the liquid composition stored in the liquid storage. And the liquid storage may be manufactured to be detachable from the vaporizer 18, or may be manufactured integrally with the vaporizer 18 as a single body.

The switch 19 sequentially transmits an amplification control signal output from the AMP 14b to the first coil 13a and the second coil 13b. The controller 12 may control opening and closing of the switch 19 so that the PWM signal may be transmitted to one of the first coil 13a and the second coil 13b. The switch 19 may be opened or closed in accordance with the PWM signal, or may be periodically opened or closed with a built-in timer. The switch 19 may be replaced with a field-effect transistor (FET), depending on the embodiment.

Figure 7:
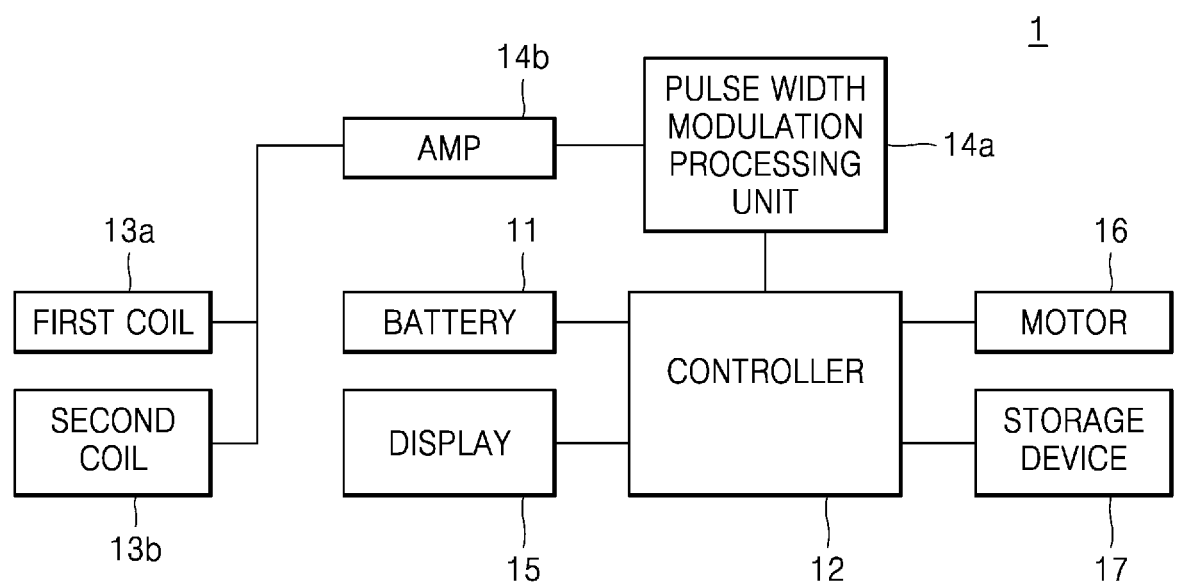
FIG. 7 is a block diagram of another example of an aerosol-generating device according to the present invention.

FIG. 7 is a block diagram of another example of an aerosol-generating device according to the present invention.

In FIG. 7, descriptions of components overlapping with FIG. 6 will be omitted.

The PWM control signal output from the pulse width modulation processing unit 14a is transmitted to the first coil 13a and the second coil 13b via the AMP 14b. Unlike the FIG. 6, the aerosol-generating device shown in FIG. 7 is not provided with a switch 19 for selectively transmitting a PWM signal to the first coil 13a or the second coil 13b. The controller 12 generates a control signal for the first coil 13a and a control signal for the second coil 13b separately, so that the PWM signal may be transmitted to the first coil 13a or the second coil 13b through the pulse width modulation processing unit 14a. Although not shown in FIGS. 6 and 7, a configuration for performing impedance matching may be added to the receiving terminals of the first coil 13a and the second coil 13b in order to maximize power supply.

The controller 12, the pulse width modulation processing unit 14a, the display 15, the storage device 17 and the vaporizer 18 in FIGS. 6 and 7 may correspond to at least one processor or may include at least one processor. Accordingly, the controller 12, the pulse width modulation processing unit 14a, the display 15, the storage device 17 and the vaporizer 18 may be driven in a form included in other hardware device such as a microprocessor or general purpose computer system.

In addition, the first coil 13a or the second coil 13b illustrated in FIGS. 6 and 7 is a simple representation of a plurality of coils. Depending on an embodiment, the number of coils included in the aerosol-generating device 1 may be more than two, and the plurality of coils may have different inductances or different number of windings per unit length.

Figure 8:
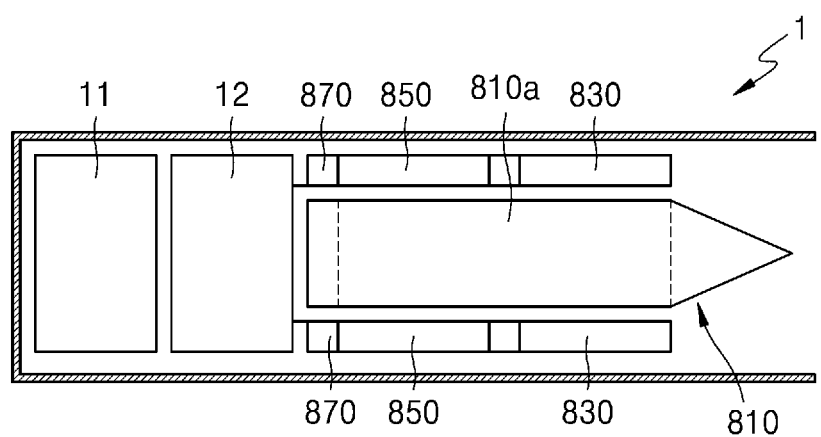
FIG. 8 is a diagram schematically showing a configuration of an aerosol-generating device according to an embodiment of the present invention.

FIG. 8 is a diagram schematically showing a configuration of an aerosol-generating device according to an embodiment of the present invention.

Referring to FIG. 8, the aerosol-generating device 1 according to an embodiment of the present invention may include a battery 11, a controller 12, a susceptor 810, a first coil 830, a second coil 850, and a bobbin 870. It is assumed that components other than those described above are omitted for convenience of description. The battery 11 and the controller 12 perform the same functions as those described with reference to FIGS. 1 to 7

The susceptor 810 is made of a material that is heated by the alternating magnetic field that is generated when the alternating current is applied to the first coil 830 and the second coil 850. The susceptor 810 refers to a material capable of converting electromagnetic energy into heat, and an eddy current induced in the susceptor 810 by an alternating magnetic field heats the susceptor 810. Here, the magnetic hysteresis loss inside the susceptor 810 additionally heats the susceptor 810. Also, when the susceptor 810 in inserted in a cigarette including an aerosol-generating substrate, as the aerosol-generating substrate of the cigarette directly or indirectly contacts the heated susceptor 810, the aerosol-generating substrate may be heated to generate an aerosol.

The susceptor 810 of FIG. 8 may consist of a susceptor heating unit 810a and the remaining portion. The susceptor heating unit 810a refers to a portion heated by the magnetic fields of the first coil 830 and the second coil 850, and may contain a susceptor material such as iron or aluminum. The remaining portion of the susceptor 810 other than the susceptor heating unit 810a may contact certain portions of the cigarette which do not include a filter or an aerosol generating-substrate. If a portion other than the susceptor heating unit 810a is heated, the filter of the cigarette may be melted or hot aerosol may be generated, thereby providing an unpleasant smoking sensation to the user. For this reasons, the remaining portion of the susceptor 810 other than the susceptor heating unit 810a does not contain a susceptor material.

The first coil 830 and the second coil 850 are supplied with alternating current under control of the controller 12 to generate an alternating magnetic field, and the magnetic field generated around the first coil 830 and the second coil 850 causes the susceptor heating unit 810a of the susceptor 810 to be heated. The principle of heating the susceptor heating unit 810a has been described above and is therefore omitted here. In addition to different physical properties of the first coil 830 and the second coil 850, the first coil 830 and the second coil 850 may be supplied with alternating currents of different magnitudes from the controller 12. As such, according to the present invention, the heating state of the susceptor heating unit 810a may be effectively controlled, and the taste of the cigarette provided to the user may be optimized. According to the present invention, by supplying a time-varying alternative current determined by experimentally or empirically accumulated data to the first coil 830 and the second coil 850, the susceptor 810 may be heated by induction heating, thereby generating aerosols.

The bobbin 870 serves as a bobbin for winding the first coil 830 and the second coil 850 smoothly.

According to the prior art, a plurality of susceptors which are made of materials having different Curie temperatures are used. If a single susceptor is used, it is difficult to uniformly heat the aerosol-generating substrate by the single coil, and thus there is a problem in that the aerosol-generating substrate is burned or the temperature control of the susceptor is not easy. However, as described in FIG. 8, according to the present invention, it is possible to uniformly heat the aerosol-generating substrate by heating a susceptor made of a single material with a plurality of coils according to induction heating, thereby providing a high quality of smoking experience to a user.

Figure 9:
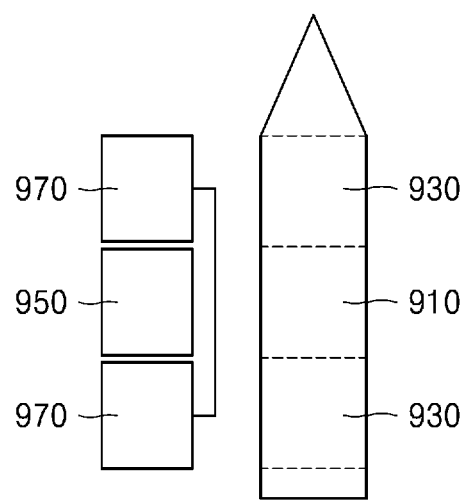
FIG. 9 is a diagram schematically showing an example of a plurality of coils and a susceptor included in the induction-heating aerosol-generating device described in FIG. 8.

FIG. 9 is a diagram schematically showing an example of a plurality of coils and a susceptor included in the induction-heating aerosol-generating device described in FIG. 8.

For convenience of description, FIG. 9 only shows a plurality of coils generating an alternating magnetic field and a susceptor heating unit 810a heated by the plurality of coils, which are shown in FIG. 8. It is assumed that other omitted components are the same as those shown in FIG. 8. In addition, hereinafter, description will be made with reference to FIG. 8. The first coil 950 and the second coil 970 receive alternating current from the controller 12 to form an alternating magnetic field.

First, the susceptor heating portion 810a includes a first heating portion 910 heated by the first coil 950 and a second heating portion 930 heated by the second coil 970. The first heating portion 910 is heated under the influence of the alternating magnetic field when an alternating magnetic field is formed by alternating current supplied to the first coil 950. The first heating portion 910 may be mainly heated under influence of the alternating magnetic field formed by the first coil 950, but may also be heated under some influence by the expansion of the alternating magnetic field formed by the second coil 970.

The second heating portion 930 is heated under the influence of the alternating magnetic field when an alternating magnetic field is formed by alternating current supplied to the second coil 970. The second heating portion 930 may be mainly heated under the influence of the alternating magnetic field formed by the second coil 970, but may also be heated under some influence by the expansion of the alternating magnetic field formed by the first coil 950. The second heating portion 930 is positioned on both sides of the first heating portion 910, and the susceptor heating portion 810a has a configuration in which the second heating portion 930, the first heating portion 910, and the second heating portion 930 are continuously connected. Here, the direction of the sides or the top and bottom with respect to the first heating portion 910 may vary depending on the orientation of the aerosol-generating device 1 including the susceptor 810.

As the first heating portion 910 and the second heating portion 930 are affected by the alternating magnetic field formed by the first coil 950 and the second coil 970, respectively, the temperature of the first heating portion 910 and the second heating portion 930 rises, and the first heating portion 910 and the second heating portion 930 are differentially heated. According to the present invention, by controlling the physical properties of the first coil 950 and the second coil 970 or the amount of alternating current flowing through the first coil 950 and the second coil 970, the first heating portion 910 and the second heating portion 930 may be heated differentially. As the aerosol-generating substrate is heated by using the above characteristics, the aerosol-generating substrate contacting the first heating portion 910 and the second heating portion 930 may be uniformly heated to generate aerosols of a consistent quality.

The first coil 950 and the second coil 970 receive alternating current under control of the controller 12 to form an alternating magnetic field. As described above, the first coil 950 effectively raises the temperature of the first heating portion 930, and the second coil 950 effectively raises the temperature of the second heating portion 930.

The second coil 970 is a coil having a specific number of windings, and does not have the same number of windings over the entire length of the coil. The second coil 970 has a predetermined interval (length) in which the number of windings is zero. More specifically, a predetermined interval in which the number of windings is zero in the second coil 970 may be determined based on the width or thickness of the first heating portion 910. Here, the number of windings of the coil is defined as the number of turns of the coil per unit length.

Further, the first coil 950 is arranged in at a predetermined interval in which the number of windings of the second coil 970 is zero. In the preheating step of heating the susceptor 810, the controller 12 controls alternating current to be supplied to both the first coil 950 and the second coil 970, such that both the first heating portion 910 and the second heating portion 930 of the susceptor heating portion 810*a* are heated to the preheating temperature. And then, when a predetermined time has elapsed after the first heating portion 910 and the second heating portion 930 reach the preheating temperature, the controller 12 determines that the susceptor 810 has entered a temperature maintenance section, and stops supplying the alternating current to the second coil 970.

In the present invention, as the controller 12 supplies alternating current only to the first coil 950 in a temperature maintenance section, it is possible to prevent melting of a filter of a cigarette and generation of overheated aerosols, which may occur when the temperature of the second heating portion 930 of the susceptor is excessively high. In addition, for convenience of explanation, the number of coils in FIG. 9 is limited to two. However, in the present invention, the number of coils is not limited to a specific number, and the number of coils may be more than two depending on an embodiment.

Figure 10:
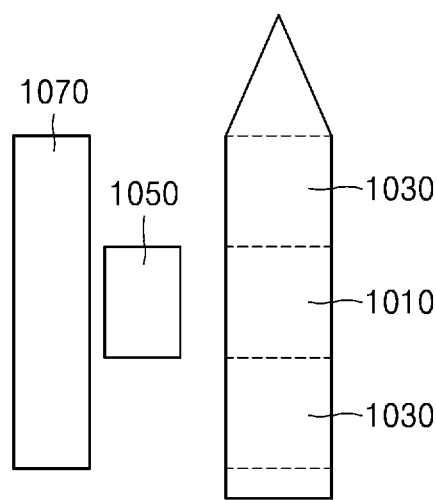
FIG. 10 is a diagram schematically showing another example of a plurality of coils and a susceptor included in the induction-heating aerosol-generating device described in FIG. 8.

FIG. 10 is a diagram schematically showing another example of a plurality of coils and a susceptor included in the induction-heating type aerosol-generating device described in FIG. 8.

For convenience of explanation, FIG. 10 only shows a plurality of coils generating an alternating magnetic field and a susceptor heating portion 810*a* heated by the plurality of coils, which are shown in FIG. 8. Other omitted components are assumed to be the same as those shown in FIG. 8. In addition, hereinafter, it will be described with reference to FIG. 8. When alternating current is applied to a first coil 1050 and a second coil 1070, the first coil 1050 and the second coil 1070 may form an alternating magnetic field.

First, the susceptor heating portion 810*a* includes a first heating portion 1010 heated by the first coil 1050 and a second heating portion 1030 heated by the second coil 1070. When alternating current is supplied to the first coil 1050 to form an alternating magnetic field, the first heating portion 1010 is heated under the influence of the alternating magnetic field. The first heating portion 1010 is heated under an influence of the alternating magnetic field formed by the first coil 1050, but may also be heated under an influence of the expansion of the alternating magnetic field formed by the second coil 1070.

In addition, when alternating current is supplied to the second coil 1070 to form an alternating magnetic field, the susceptor heating portion 810*a* including both the first heating portion 1010 and the second heating portion 1030 is heated under the influence of the alternating magnetic field. The controller 12 allows the alternating current to flow simultaneously through the first coil 1050 and the second coil 1070, so that the susceptor heating portion 810*a* rapidly reaches the preheating temperature. And then, the controller 12 may induce that only the first heating portion 1010 is continuously heated by blocking the alternating current supplied to the second coil 1070. Through this process, the first heating portion 1010 is affected by both the alternating magnetic field formed by the first coil 1050 and the alternating magnetic field formed by the second coil 1070. In the present exemplary embodiment, the coil heating the first heating portion 1010 may be understood as an equivalent coil in which the numbers of windings of the first coil 1050 and the second coil 1070 are overlapped or summed. In addition, although the number of the plurality of coils is limited to two in FIG. 10, depending on the embodiment, the number of coils may be more than two.

Figure 11:
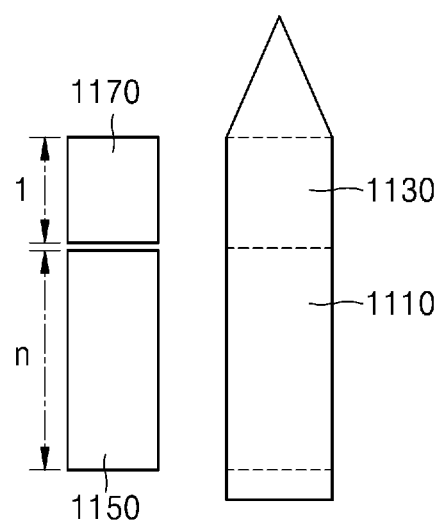
FIG. 11 is a diagram schematically showing another example of a plurality of coils and a susceptor included in the induction-heating aerosol-generating device described in FIG. 8.

FIG. 11 is a diagram schematically showing another example of a plurality of coils and a susceptor included in the induction-heating type aerosol-generating device described in FIG. 8.

For convenience of description, FIG. 11 only shows a plurality of coils that generate an alternating magnetic field and a susceptor heating portion 810*a* heated by the plurality of coils as shown in FIG. 8. Other omitted components are assumed to be the same as those shown in FIG. 8. In addition, hereinafter, it will be described with reference to FIG. 8, a first coil 1150 and a second coil 1170, when alternating current is applied, may form an alternating magnetic field. First, the susceptor heating portion 810*a* includes a first heating portion 1110 heated by the first coil 1150 and a second heating portion 1130 heated by the second coil 1170. When alternating current is supplied to the first coil 1150 to form an alternating magnetic field, the first heating portion 1110 is heated under an influence of the alternating magnetic field. Here, the first heating portion 1110 may also be heated under an influence of the expansion of the alternating magnetic field formed by the second coil 1170.

In addition, when alternating current is supplied to the second coil 1170 to form an alternating magnetic field, the second heating portion 1130 is heated under the influence of the alternating magnetic field. The length ratio of the first coil 1150 and the second coil 1170 is n:1, where n may be any real number determined mathematically or experimentally. Here, the length of the coil means the length of the coil itself in the coiled state, and does not mean the length of a metal wire state that is in an uncoiled state, which should not be called a coil.

According to a known formula for calculating the strength of the magnetic field of a solenoid coil, when the number of windings per portion length is changed, the strength of the magnetic field generated by alternating current flowing in the coil is also changed. By changing the number n appropriately, the heating speeds of the first heating portion 1110 and the second heating portion 1130 also changes according to the physical properties of the first coil 1150 and the second coil 1170. As illustrated in FIGS. 9 and 10, the controller 12 may simultaneously heat the first heating portion 1110 and the second heating portion 1130, and then stop supplying the alternating current to the second coil 1170. When the supply of the alternating current to the second coil 1170 is stopped, the second heating portion 1130 may be heated at a much slower speed than the speed at which the first heating portion 1110 is heated, by a conduction heat of the first heating portion 1110 or by the expansion of the alternating magnetic field formed by the first coil 1150.

According to this exemplary embodiment, by adjusting the number n to adjust the heating speeds of the first heating portion 1110 and the second heating portion 1130 differently, the aerosol-generating substrate contacting the susceptor heating portion 810*a* may be heated according to desired characteristics. In this exemplary embodiment, the ratio of the length of the second coil 1170 to the length of the first coil 1150 may be equal to or less than a preset value. Here, the ratio of the length of the second coil 1170 to the length of the first coil 1150 is 1/n when shown with reference to FIG. 11.

Figure 12:
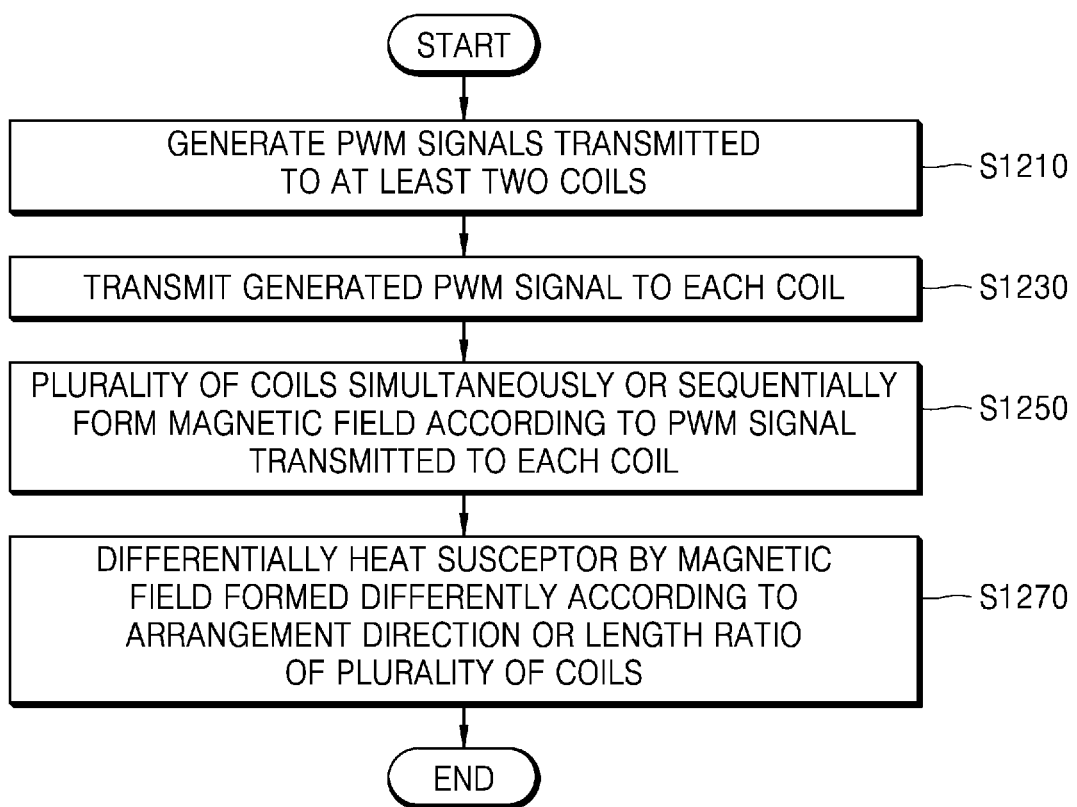
FIG. 12 is a flowchart illustrating an example of a method of generating an aerosol using induction heating according to the present invention.

FIG. 12 is a flowchart illustrating an example of a method of generating an aerosol using an induction heating method according to the present invention.

The aerosol-generating method shown in FIG. 12 may be implemented by the aerosol-generating device according to FIGS. 1, 2, 3, 6 and 7. Hereinafter, the aerosol-generation method will be described with reference to FIGS. 1, 2, 3, 6, and 7, and the description overlapping with the above description will be omitted.

In step S1210, the controller 12 controls to generate PWM signals transmitted to at least two coils. After generating the control signal, the controller 12 may generate PWM control signals by transmitting a control signal to the pulse width modulation processing unit 14 located inside or outside the controller 12.

In step S1230, the PWM signals generated in step S1210 are transmitted to a plurality of coils, respectively.

In step S1250, a plurality of coils receiving the PWM signals form alternating magnetic fields simultaneously or sequentially.

In step S1270, the susceptor 810 provided in the aerosol-generating device 1 is differentially heated by a magnetic field formed differently according to the arrangement direction or a length ratio of the plurality of coils. When the cigarette containing the aerosol-generating substrate contacts the susceptor heated differentially in step S1270, the aerosol-generating substrate is differentially heated, so that the properties of the generated aerosols may be variously adjusted. According to the present invention, the user may inhale aerosols that provide an optimized feeling of smoking.

Those of ordinary skill in the art related to this embodiment will understand that it may be implemented in a modified form without departing from the essential characteristics of the above-described substrate. The disclosed methods should be considered in a descriptive sense only and not for purposes of limitation. The scope of the present invention is shown in the claims rather than the foregoing description, and all differences within the equivalent scope should be interpreted as being included in the present invention.

INDUSTRIAL APPLICABILITY

The present invention may be utilized to manufacture next-generation electronic cigarettes that may provide convenience for users and provide a consistent smoking experience.

What is claimed is:

1. An aerosol-generating device using induction heating, comprising:
   a plurality of coils having different numbers of windings and configured to generate alternating magnetic fields based on an alternating current;
   a susceptor configured to generate an aerosol by heating adjacent aerosol-generating substrates using heat generated through the alternating magnetic fields generated from the plurality of coils; and
   a controller,
   wherein the plurality of coils comprises a first coil corresponding to a first portion of the susceptor and a second coil corresponding to a second portion of the susceptor, and
   wherein the controller is configured to control the alternating current to be supplied to the first coil and the second coil, such that the first portion and the second portion of the susceptor are heated differentially by the alternating current.

2. The aerosol-generating device of claim 1, wherein
   the susceptor further includes a third portion in addition to the first portion and the second portion,
   the first portion, the second portion, and the third portion are continuously connected, and the plurality of coils are arranged such that the first portion and the third portion are differentially heated from the second portion.

3. The aerosol-generating device of claim 2, wherein
   the first portion and the third portion are heated by an alternating magnetic field generated from the first coil having a predetermined interval with zero windings, and
   the second portion is heated by an alternating magnetic field generated from the second coil arranged in the predetermined interval.

4. The aerosol-generating device of claim 3, wherein the controller is configured to stop supplying the alternating current to the first coil when a predetermined time has elapsed after the alternating current is supplied to the first coil and the second coil.

5. The aerosol-generating device of claim 1, wherein at least two of the plurality of coils are arranged to overlap in a specific direction from the first portion so that the first portion is heated according to alternating magnetic fields generated by the at least two coils.

6. The aerosol-generating device of claim 1, wherein a ratio of a length of the second coil to a length of the first coil is equal to or less than a preset value.

7. The aerosol-generating device of claim 1, wherein the controller is configured to control the alternating current to be supplied to the plurality of coils at different time points through a field-effect transistor (FET).

8. A method of generating an aerosol, the method comprising:
   generating alternating magnetic fields by a controller controlling an alternating current to be supplied to a plurality of coils having different winding numbers; and
   heating an adjacent aerosol-generating substrate by a susceptor that is inductively heated by the alternating magnetic fields,
   wherein the plurality of coils comprises a first coil corresponding to a first portion of the susceptor and a second coil corresponding to a second portion of the susceptor, and
   wherein the heating the adjacent aerosol-generating substrate includes differentially heating the first portion and the second portion of the susceptor by the alternating current supplied to the first coil and the second coil.

9. The method of claim 8, wherein
   the susceptor further includes a third portion in addition to the first portion and the second portion,
   the first portion, the second portion, and the third portion are continuously connected, and
   the heating the adjacent aerosol-generating substrate includes the first coil and heating the first portion and the third portion differentially from the second coil heating the second portion.

10. The method of claim 9, wherein the heating of the adjacent aerosol-generating substrate includes:

heating the first portion and the third portion based on the alternating current being supplied to the first coil having a predetermined interval with zero windings; and heating the second portion based on the alternating current being supplied to the second coil arranged in the predetermined interval.

11. The method of claim 10, further comprising stopping supply of the alternating current to the first coil when a predetermined time has elapsed after the alternating current is supplied to the first coil and the second coil.

12. The method of claim 8, wherein the heating of the adjacent aerosol-generating substrate includes heating the first portion according to the alternating magnetic fields generated by the plurality of coils arranged to overlap in a specific direction from the first portion.

13. The method of claim 8, wherein
a ratio of a length of the second coil to a length of the first coil is equal to or less than a preset value.

14. The method of claim 8, wherein the generating of the alternating magnetic fields includes supplying the alternating current to the plurality of coils at different time points through a field-effect transistor (FET).

* * * * *